United States Patent
Tortelli et al.

(10) Patent No.: US 6,703,521 B2
(45) Date of Patent: Mar. 9, 2004

(54) ALKYL ESTERS OF THE 2-(2-FLUOROSULPHONYL)-PERFLUOROETHYLENOXY-3-HALOGEN-PROPIONIC ACID

(75) Inventors: Vito Tortelli, Milan (IT); Sara Maculan, Varese (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 10/329,710

(22) Filed: Dec. 27, 2002

(65) Prior Publication Data

US 2003/0125582 A1 Jul. 3, 2003

(30) Foreign Application Priority Data

Jan. 3, 2002 (IT) .................................. MI2002A000001

(51) Int. Cl.⁷ .......................... C07C 315/00; C07C 69/35
(52) U.S. Cl. ........................................ 560/150; 560/227
(58) Field of Search ................................ 560/129, 226, 560/227, 147, 150

(56) References Cited

U.S. PATENT DOCUMENTS

| 2,713,593 | A | 7/1955 | Brice et al. |
| 4,358,412 | A | 11/1982 | Ezzell et al. |
| 4,801,409 | A | 1/1989 | Marraccini et al. |
| 4,962,282 | A | 10/1990 | Marraccini et al. |
| 5,488,142 | A | 1/1996 | Fall et al. |

FOREIGN PATENT DOCUMENTS

| EP | 0041736 A | 12/1981 |
| EP | 1225167 A1 | 7/2002 |
| GB | 2029827 A | 3/1980 |
| JP | 11228474 A | 8/1999 |
| WO | WO 98/50603 | 11/1998 |

OTHER PUBLICATIONS

England et al., "Reactions of Fluoroölefins with Sulfur Trioxide", J. Amer. Chem. Soc., vol. 82, pp. 6181–6188, 1960.

Primary Examiner—Johann Richter
Assistant Examiner—Karl J. Pultlitz
(74) Attorney, Agent, or Firm—Arent Fox Kintner Plotkin & Kahn, PLLC

(57) ABSTRACT

Compounds of formula $CH_2Y-CH(COOR_1)-O-CF_2CF_2-SO_2F$, usable in the synthesis of the fluorosulphonic vinylether $-CF_2=CF-O-CF_2CF_2-SO_2F$.

2 Claims, No Drawings

ALKYL ESTERS OF THE 2-(2-FLUOROSULPHONYL)-PERFLUOROETHYLENOXY-3-HALOGEN-PROPIONIC ACID

The present invention relates to a class of compounds to be used for the preparation of linear fluorinated vinylethers containing one fluorosulphonic group, and the preparation process thereof.

It is well known that fluorosulphonic vinylethers form a class of monomers useful for obtaining polymers containing $-SO_2F$ groups, which are used in electrochemical applications as membranes for chloro-soda cells, fuel cells or as acid catalysts in organic synthesis.

Compounds usable for the preparation of fluorosulphonic vinylethers are known in the prior art.

U.S. Pat. No. 4,358,412 describes the synthesis of the fluorosulphonic vinylether $CF_2=CF-O-CF_2CF_2-SO_2F$, wherein in the first step the compound $$FOC-CF(CF_2Cl)-O-(CF_2)_2SO_2F \quad (I)$$

is obtained by reacting the acylfluoride $FOC-CF_2-SO_2F$ with the perfluoroallylchloride epoxide. In the second step the alkaline pyrolysis is carried out with sodium carbonate obtaining the fluorosulphonic vinylether. The synthesis of the formula (I) compound has the drawback to use the perfluoroallychloride epoxide which is very expensive and not easily available.

U.S. Pat. Nos. 4,962,282 and 4,801,409 describe the synthesis in gaseous phase of the hypofluorite $FSO_2CF_2CF_2OF$ starting, respectively, from the tetrafluoroethylene β sultone having the formula:

or from the acylfluoride $FSO_2CF_2COF$.

The sulphonic hypofluorite $FSO_2CF_2CF_2OF$ can then be added, according to the prior art, to 1,2-dichloro-1,2-difluoroethylene, and then by dechlorination the monomer $CF_2=CF-O-CF_2CF_2-SO_2F$ is obtained. The sulphonic hypofluorite used in said process has the drawback to be a strongly oxidizing agent which requires particular precautions.

The need was felt to have available a class of compounds usable in the synthesis of the fluorosulphonic vinylether $CF_2=CF-O-CF_2CF_2-SO_2F$, obtainable from easily available reactants, using the usual laboratory techniques.

A class of compounds which solves the above technical problem has been found.

An object of the present invention is a class of compounds, usable for the preparation of the fluorosulphonic vinylether $CF_2=CF-O-CF_2CF_2-SO_2F$, formed by alkyl esters of the 2-(2-fluorosulphonyl) perfluoroethylenoxy-3-halogen-propionic acid, having the following formula (II):

$$CH_2Y-CH(COOR_1)-O-CF_2CF_2-SO_2F \quad (II)$$

wherein:
Y=Cl, Br;
$R_1=C_1-C_4$ linear or branched alkyl.
Preferably in formula (II) Y=Cl and $R_1$=methyl.

The invention compounds are obtainable by the following process:
a) synthesis of the alcoholate of formula $MOCF_2CF_2-SO_2F$, wherein M=K, Cs, Ag, by reaction between MF and TFE β-sultone

or by reaction between MF and the acylfluoride $FOC-CF_2-SO_2F$;

b) reaction between a compound of formula $CH_2Y-CHX-COOR_1$ (III), wherein:
Y and $R_1$ are as above;
X=Cl, Br; Y and X being equal or different, with the proviso that when Y=Br X=Br;
with the alcoholate obtained in step a) according to the following scheme:

$$MOCF_2CF_2-SO_2F + CH_2Y-CHX-COOR_1 \longrightarrow$$
$$MX + CH_2Y-CH(COOR_1)-O-CF_2CF_2-SO_2F.$$

The step a) is carried out in an aprotic dipolar solvent, for example diglyme (diethylen glycol dimethylether), acetonitrile, at temperatures in the range 20° C.–50° C.; the β-sultone can be synthesized as described by England et Al. J. Am. Chem. Soc. 82 6181 1960.

The step b) is carried out at temperatures in the range 20° C.–80° C., by directly adding the alkyl halide RX to the reaction mixture obtained at the end of step a); at the end of the reaction it is distilled at reduced pressure and subsequently the distillate is extracted with water, the organic phase is separated and dried, recovering the product by solvent evaporation.

The invention results are surprising and unexpected since the reaction in step b) takes place selectively on the secondary carbon atom, bound to X in the formula (III) compound and it does not involve the primary carbon, bound to Y or that of carbonyl of the $COOR_1$ group. This is surprising since one could expect that the reaction led to a product mixture, forming in low yields the final product. Surprisingly it has been found that said secondary reactions substantially do not take place and that the formula (II) compound is obtained in high yields. Furthermore the formula (II) compound is easily recovered from the reaction mixture.

The RX compounds are easily accessible and can be obtained by halogenation of acrylic esters.

As said, the invention compounds are usable for the synthesis of the fluorosulphonic vinylether of formula: $CF_2=CF-O-CF_2CF_2-SO_2F$.

For example, the synthesis comprising the following steps can be used:
1) fluorination of the formula (II) compound to give the acylfluoride $CF_2YCF(COF)OCF_2CF_2-SO_2F$;
2) saponification of the acylfluoride to the corresponding carboxylate $CF_2YCF(COO^-Me^+)OCF_2CF_2-SO_2F$, wherein $Me^+$ is the alkaline metal cation;
3) thermal decomposition of the carboxylate obtained in 2) and formation of the fluorosulphonic vinylether.

The step 1) fluorination is carried out either by electrochemical fluorination or by direct fluorination. The electrochemical fluorination is described in U.S. Pat. No. 2,713,593 and in patent application WO 98/50603. The direct fluorination is described in U.S. Pat. No. 5,488,142.

For example a tubular reactor, as described in U.S. Pat. No. 5,488,142, can be used for the direct fluorination, by adding the formula (II) compound to a circulating liquid flow of an inert solvent, for example perfluorohexane, to which elemental fluorine diluted with nitrogen is continuously fed at the temperature of 20° C.

The acylfluoride saponification in step 2) is carried out by treatment with alkales at room temperature (20°–25° C.).

Step 3) of the thermal decomposition is carried out by heating the compound isolated at the end of step 2) at a temperature in the range 50° C.–220° C., optionally dispersed in a solvent having a boiling point higher than that of the reaction product, inert under the reaction conditions, by distilling the formed fluorosulphonic vinylether.

The following Examples illustrate the invention and do not limit the scope thereof.

EXAMPLE 1

In a two-necked 50 ml glass flask, equipped with condenser, tap for nitrogen and magnetic stirrer, 2.14 g (0.017 moles) of silver fluoride are introduced in dry box.

Subsequently 5 ml of fresh distilled diglyme (diethylen glycol dimethylether) are fed under nitrogen atmosphere. The mixture is cooled at −78° C. and then a solution at 14.5% by weight of β sultone

in CFC 113 ($CFCl_2CF_2Cl$) (3.04 g, 0.017 moles of β sultone) is added. The mixture is brought to room temperature and heated at 33° C. for 2 hours and 30 minutes. CFC 113 is removed at reduced pressure, the mixture is cooled again at −78° C. and 2.65 g (0.017 moles) of 2,3-dichloro-methyl propionate are added.

The mixture is heated at 42° C. for 8 hours and at the end the reaction mixture is distilled at reduced pressure (residual pressure of about 20 mm Hg, corresponding to $2.67 \times 10^3$ Pa) gradually increasing the mixture temperature up to 80° C. The obtained mixture is extracted with 15 ml of water. The organic phase is separated, washed three times with water and dried with $P_4O_{10}$. 2.23 g of $ClCH_2CH(OCF_2CF_2SO_2F)COOCH_3$ ($^{19}$FNMR) are obtained. Yield 41%.

EXAMPLE 2

In the equipment of Example 1 and with the same operating procedure 2.51 g (0.017 moles) of anhydrous CsF are introduced.

Subsequently 6 ml of fresh distilled diglyme are fed under nitrogen atmosphere. The mixture is cooled at −78° C. and then 3.2 g (0.018 moles) of acylfluoride $FSO_2CF_2COF$ are added. The mixture is brought to room temperature and heated at 35° C. for 1 hour and 30 minutes; the mixture is cooled again at −78° C. and 2.4 g (0.015 moles) of 2,3-dichloro-methyl propionate are added.

The mixture is heated at 55° C. for 18 hours and 30 minutes and lastly the reaction mixture is distilled at reduced pressure (residual pressure of about 20 mm Hg, corresponding to $2.67 \times 10^3$ Pa) gradually increasing the mixture temperature up to 80° C. The obtained mixture is extracted with 15 ml of water. The organic phase is separated, washed three times with water and dried with $P_4O_{10}$. 1.9 g of $ClCH_2CH(OCF_2CF_2SO_2F)COOCH_3$ ($^{19}$FNMR) are obtained. Yield 39% (calculated on 2,3-dichloromethyl propionate).

What is claimed is:

1. Compounds of the following formula (II):

wherein:

Y is Cl or Br; and $R_1$ is $C_1$–$C_4$ linear or branched alkyl.

2. Compounds according to claim 1, wherein in formula (II) Y is Cl and $R_1$ is methyl.

* * * * *